United States Patent [19]
Astle

[11] Patent Number: 5,470,744
[45] Date of Patent: Nov. 28, 1995

[54] BIOASSAY INCUBATOR FOR USE WITH ROBOTIC ARMS

[76] Inventor: Thomas W. Astle, 607 Harborview Rd., Orange, Conn. 06477

[21] Appl. No.: 227,712

[22] Filed: Apr. 14, 1994

[51] Int. Cl.$^6$ .............................. C12M 1/00; C12M 1/38
[52] U.S. Cl. .................... 435/286.7; 435/303.3; 435/305.3; 435/305.4; 435/809; 422/64; 160/241
[58] Field of Search ................... 435/287, 289, 435/290, 300, 301, 310, 312, 316, 809; 422/64; 432/250; 34/202, 242, 201; 414/217, 222; 219/385, 386, 388, 389; 221/150 R, 150 AC, 150 A; 126/190; 160/85, 120, 122, 241, 237, DIG. 8; 62/265, 266, 381, 458

[56] References Cited

U.S. PATENT DOCUMENTS

| | | | |
|---|---|---|---|
| 1,539,774 | 5/1925 | Sato | 160/241 |
| 2,811,201 | 10/1957 | Reid | 160/122 |
| 2,897,888 | 8/1959 | Dragonuk | 160/122 |
| 4,118,280 | 10/1978 | Charles et al. | 435/809 |
| 4,250,266 | 2/1981 | Wade | 435/809 |
| 4,766,941 | 8/1988 | Sloop et al. | 160/241 |
| 5,052,459 | 10/1991 | Grossenbacher | 160/85 |

Primary Examiner—William H. Beisner
Attorney, Agent, or Firm—John H. Crozier

[57] ABSTRACT

In a preferred embodiment, a bioassay incubator for use with a robotic arm, the incubator including: a housing; a first plurality of linearly spaced apart shelves disposed within the housing, the shelves dimensioned to support thereon bioassay trays; a robotic access opening defined in the housing and extending along the first plurality of shelves, through which robotic access opening the first plurality of shelves may be accessed by a robotic arm to place on, or to remove from, the bioassay trays; sealing apparatus disposed over and substantially sealing the robotic access opening; and the sealing apparatus having defined therethrough a robotic access window, the robotic access window being positionable adjacent a selected one of the first plurality of shelves and being minimally dimensioned to permit the robotic arm to assess the selected one of the shelves therethrough, while the sealing apparatus otherwise substantially seals the robotic access opening to minimize disturbance of the interior environment of the incubator.

6 Claims, 8 Drawing Sheets

BIOASSAY INCUBATOR FOR USE WITH ROBOTIC ARMS

BACKGROUND OF THE INVENTION

1. Field of the Invention

The present invention relates to biological assay systems generally and, more particularly, but not by way of limitation, to a novel biological assay incubator for access by robotic arms, with minimum interruption of the internal environment of the incubator.

2. Background Art

In the field of biological assays, there is a need to hold the test reagents at various temperatures for various lengths of time. This is commonly done in an incubator. The incubator may be hot or cold, depending on the requirements of the assay. In addition to temperature, other environmental conditions may also require control. For example, cell cultures may need a carbon dioxide rich environment. Fermentations may require an excess of oxygen. Many tests are processed in microplates at small working volumes which may be 50 microliters to 200 microliters per well, for example. At these small volumes, evaporation is a concern. Thus, humidity control is often required. Control of any or all of these elements may be incorporated into, and is available in, the incubators on the market at the present time.

As the field of biotechnology research advances, there is an increasing need to run higher numbers of tests. This need is being met with fully automated systems, utilizing robotic arms to transfer test plates from one device to another. The use of robotic arms places additional requirements on the design of the incubators, since a robotic arm must access predefined positions. These positions must be within the reach of the arm, which is often limited by economics, since the size required for the accessible space determines the system cost. Robotic arm systems are commonly used in one of two formats: they are either mounted on a pivot or on a linear track. A pivot mounted arm can access anything within the cylindrical area described by the arm's radius and its vertical reach. A track mounted arm can serve the aisle on both sides of the track. The length of the aisle, of course, is determined by track length, which, again, is a function of economics and available space. In either case, it is desirable to conserve the arm's accessible real estate.

In addition to considerations of economics, a particular problem with conventional robotic arm systems for use with bioassay incubators is that, when the robotic arms access the interiors of the incubators, which occurs periodically and frequently, there is considerable disturbance of the interior environments of the incubators, often through the opening of large areas of the sides of the incubators. This disturbance interferes with temperature, humidity, and/or gas composition control.

Accordingly, it is a principal object of the present invention to provide a bioassay incubator for use with a robotic arm, which incubator provides for a relatively large, yet compact, accessible space for the robotic arm.

It is a further object of the invention to provide such an incubator which permits control of the interior environment of the incubator without significant interference with that environment when the interior of the incubator is accessed by the robotic arm.

It is an additional object of the invention to provide such an incubator which can be simply and economically constructed.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a bioassay incubator for use with a robotic arm, said incubator comprising: a housing; a first plurality of linearly spaced apart shelves disposed within said housing, said shelves dimensioned to support thereon bioassay trays; a robotic access opening defined in said housing and extending along said first plurality of shelves, through which robotic access opening said first plurality of shelves may be accessed by a robotic arm to place on, or to remove from, said bioassay trays; sealing means disposed over and substantially sealing said robotic access opening; and said sealing means having defined therethrough a robotic access window, said robotic access window being positionable adjacent a selected one of said first plurality of shelves and being minimally dimensioned to permit said robotic arm to assess said selected one of said shelves therethrough, while said sealing means otherwise substantially seals said robotic access opening to minimize disturbance of the interior environment of said incubator.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

Figure 1:
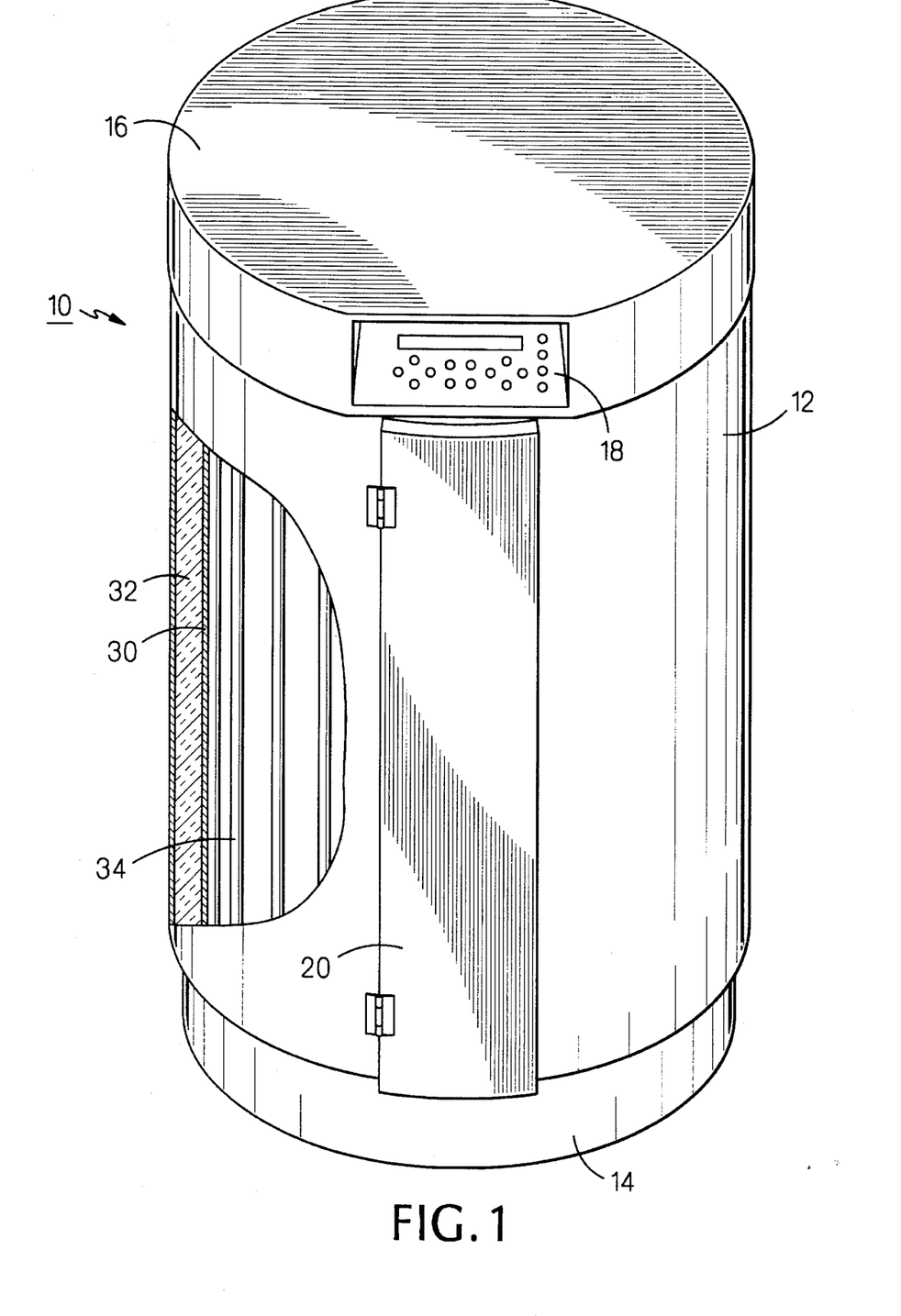
FIG. 1 is a rear isometric view, partially cutaway, of an incubator constructed according to the present invention, showing a manual access door and a control panel.

FIG. 1 illustrates the rear of a bioassay incubator, constructed according to the present invention, and generally indicated by the reference numeral 10. Incubator 10 includes a cylindrical outer shell 12 mounted on, and supported by, a cylindrical base 14. A lid 16 covers the top of outer shell 12 and has mounted therein a control panel 18 which provides the necessary interface between the operator of incubator 10 and the system controls (not shown) for the incubator. A hinged, manual access door 20 is provided along the full length of outer shell 12 for manually access to the interior of the housing. A cylindrical inner shell 30 is disposed parallel to and spaced from outer shell 12 and the annulus defined therebetween is filled with a suitable thermal insulation material 32. A plurality of heat transfer coils, as a 34, is attached to the outer surface of inner shell 30. Since temperature has a direct effect on the growth of many cells and organisms, it is important that the interior temperature of incubator 10 be uniform and precisely maintained. Insulation 32 and heat transfer coils 34 meet this requirement. A heat transfer coil (not shown) can also be provided in the center core. A heat transfer medium can then be circulated through these coils. The enclosed unit may run as an incubator at elevated temperatures, such as about thirty-seven degrees Centigrade, or as a refrigerator at lower temperatures, such as about four degrees Centigrade. Conventional temperature control systems can be used to maintain the desired temperature.

Figure 2:
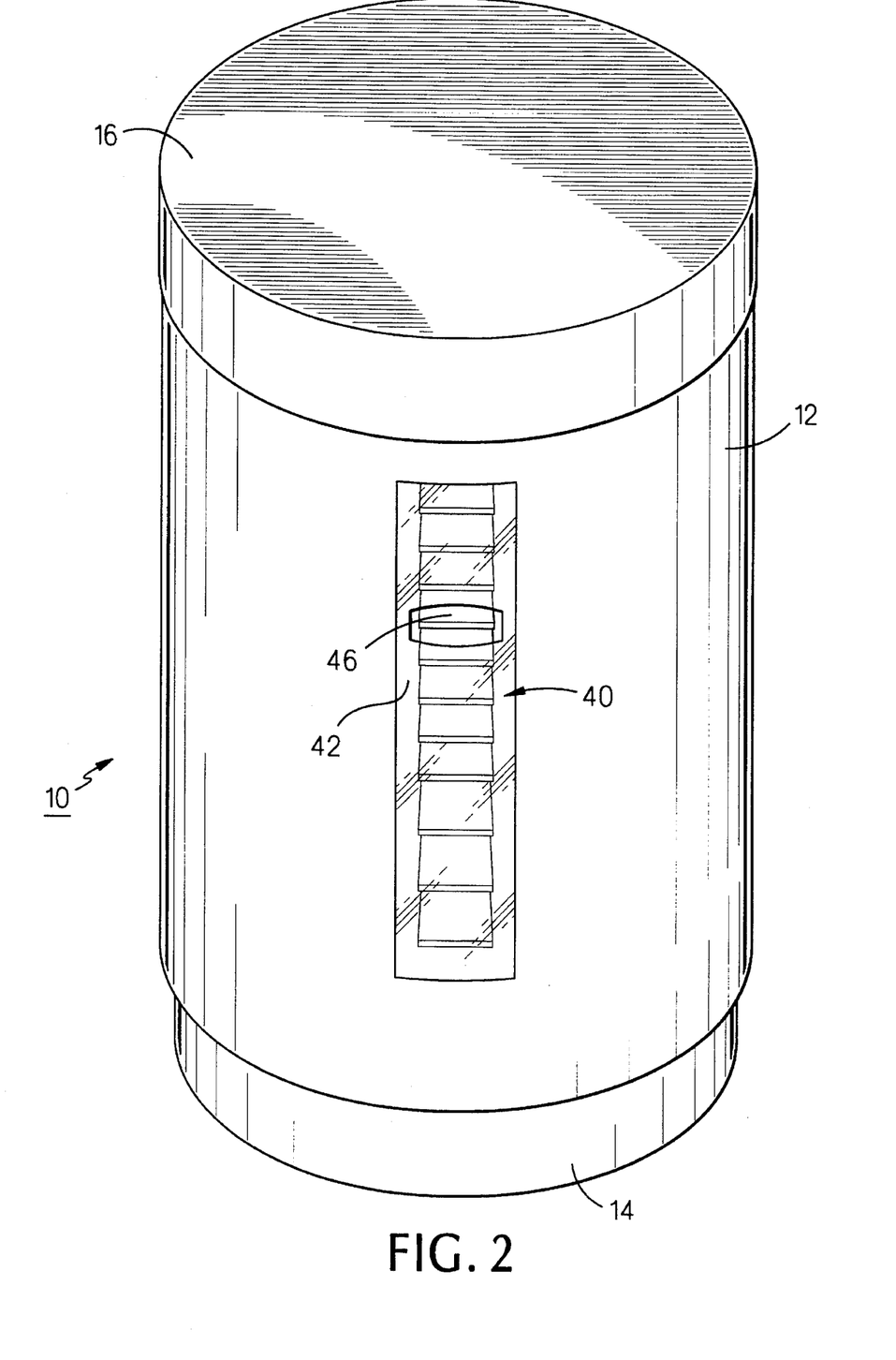
FIG. 2 is a front isometric view of the incubator, showing a robotic access window with a sealing curtain thereover.

As illustrated on FIG. 2, a vertical robotic access opening 40 extends nearly the full length of outer shell 12 and is covered by a traveling polyester curtain 42 which has a robotic access window 44 defined therethrough. Robotic access window 44 is provided so that a robotic hand (not shown) can make access through this window to reach a selected one of a plurality of storage shelves, as at 46, disposed within incubator 10 and is minimally dimensioned therefor to minimize the disturbance of the interior environment of incubator 10.

Figure 3:
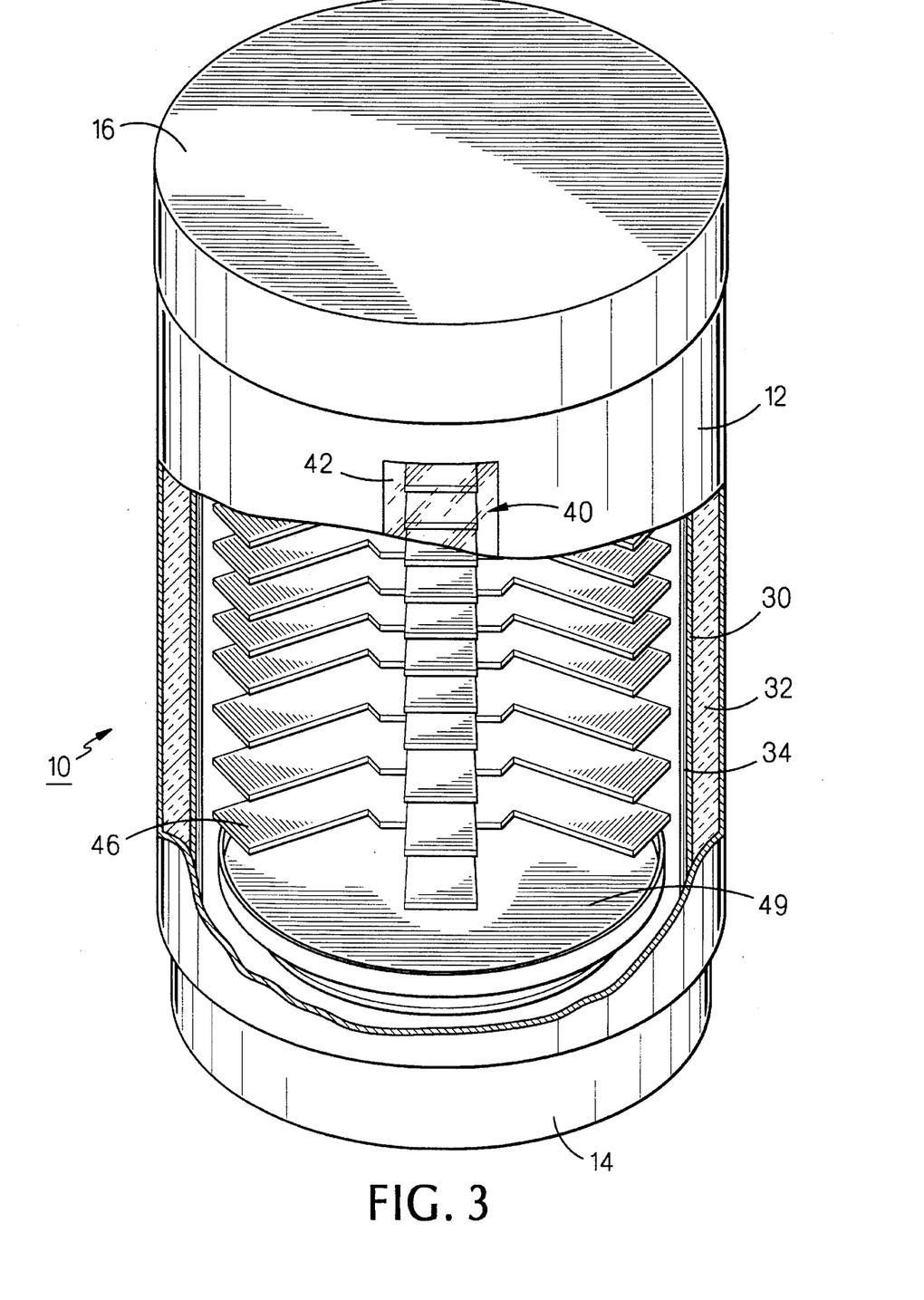
FIG. 3 is a cutaway front isometric view of the incubator, showing the interior shelf arrangement thereof.
Figure 4:
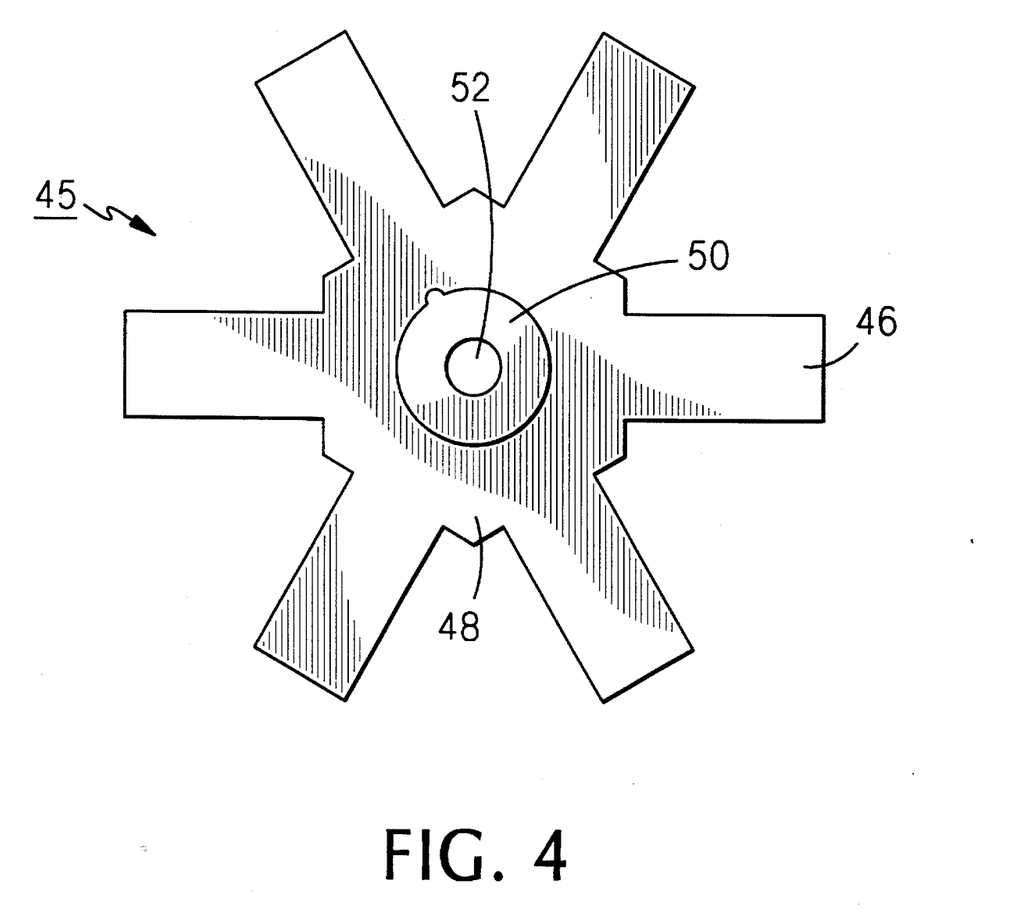
FIG. 4 is a top plan view of the shelf assembly of FIG. 3.

Referring to FIGS. 3 and 4 together, an interior shelf arrangement of incubator 10 consists of stacked independent shelf assemblies, as at 45, each shelf assembly comprising six horizontal shelves 46 extending outwardly from an integral hexagonal plate 48 (FIG. 4) which is keyed to a cylindrical, vertical, rotatable drive column 50 which rotates about a central, vertical support column 52. Each shelf 46 is sized to support thereon an assay plate (not shown). A large open pan 49 (FIG. 3) is provided below shelf assemblies 45 to which pan water may be added to control the humidity in incubator 10. To accelerate evaporation from pan 49, a separate heater assembly (not shown) may be located on the underside surface of the pan. The heat supplied to pan 49 is controlled by a relative humidity sensor (not shown). As the relative humidity in incubator 10 drops below a selected set point, heat is applied to pan 49. As the humidity in incubator 10 reaches its set point, the heat to pan 49 is correspondingly diminished.

Figure 5:
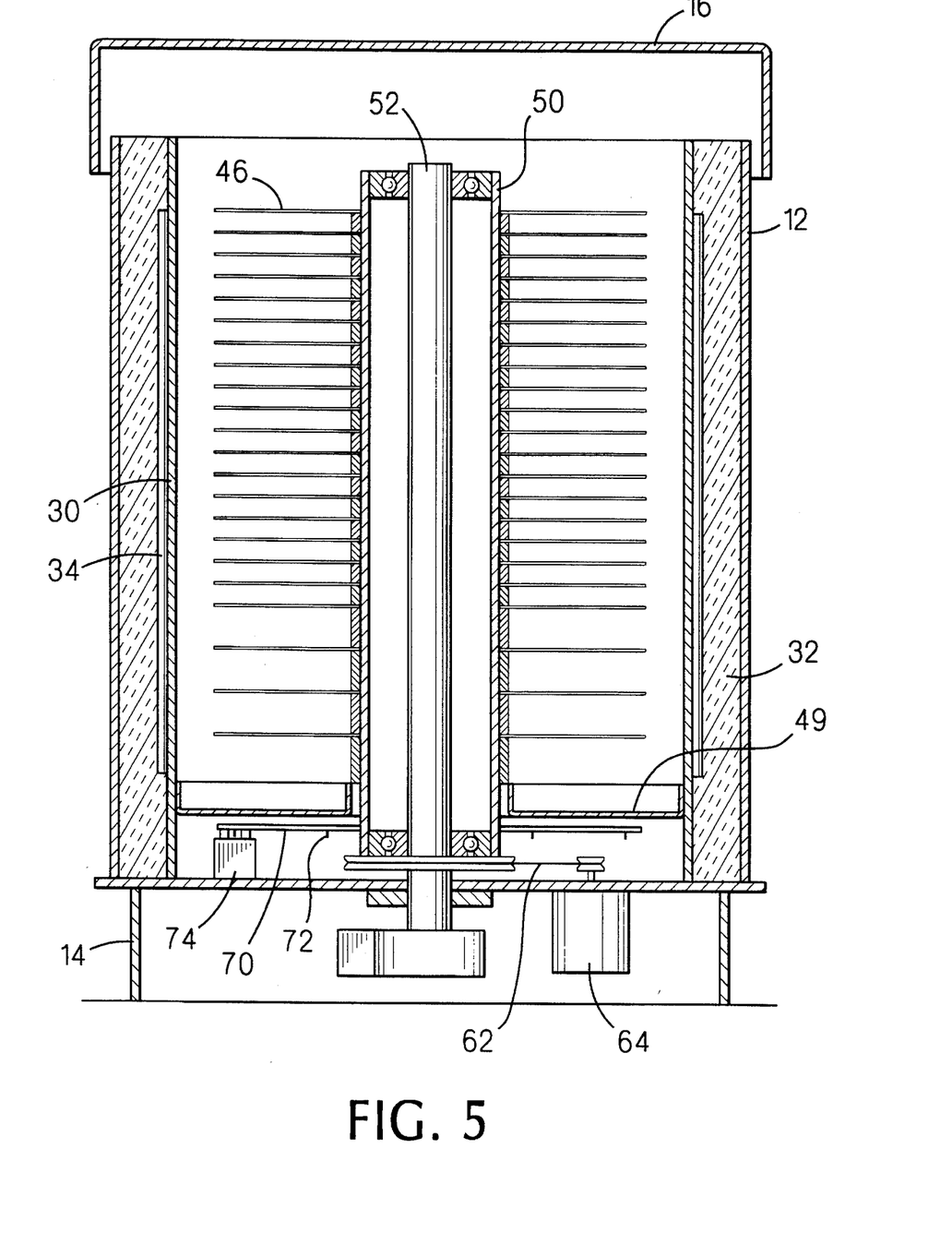
FIG. 5 is a partially schematic, cross-sectional elevational view of the incubator, showing the drive system and shelf spacing thereof.

Referring also to FIG. 5, shelf assemblies 45 are stacked around drive column 50 with spacer rings, as at 60, therebetween to provide adjustable spacing to meet various assay requirements. While most assays use a standard microplate, some assays require higher working volumes. This need is met by using deep well plates. To accommodate the difference in height, different height spacer rings 60 may be employed to vary the vertical distance between shelf assemblies 45 for the requirements of the user, as is indicated on FIG. 5.

Drive column 50 is connected by a chain or belt drive 62 to a stepper type drive motor 64. By means of a microprocessor based control system (not shown), drive motor 64 can precisely position any column of shelves on the centerline of robotic access opening 40.

Referring especially to FIG. 5, a large diameter decoder disc 70 has six vertical pins, as at 72, depending from the lower surface of the disc and located on the centerline of each column of shelves 46. Pins 72 break the light path between a photodiode and a phototransistor on photodetector 74 to provide a position signal to the control circuit (not shown). Pins 72 and the control circuit can be arranged to provide a binary code at each position, providing absolute encoding, or they can provide incremental encoding from a home position.

Figure 7:
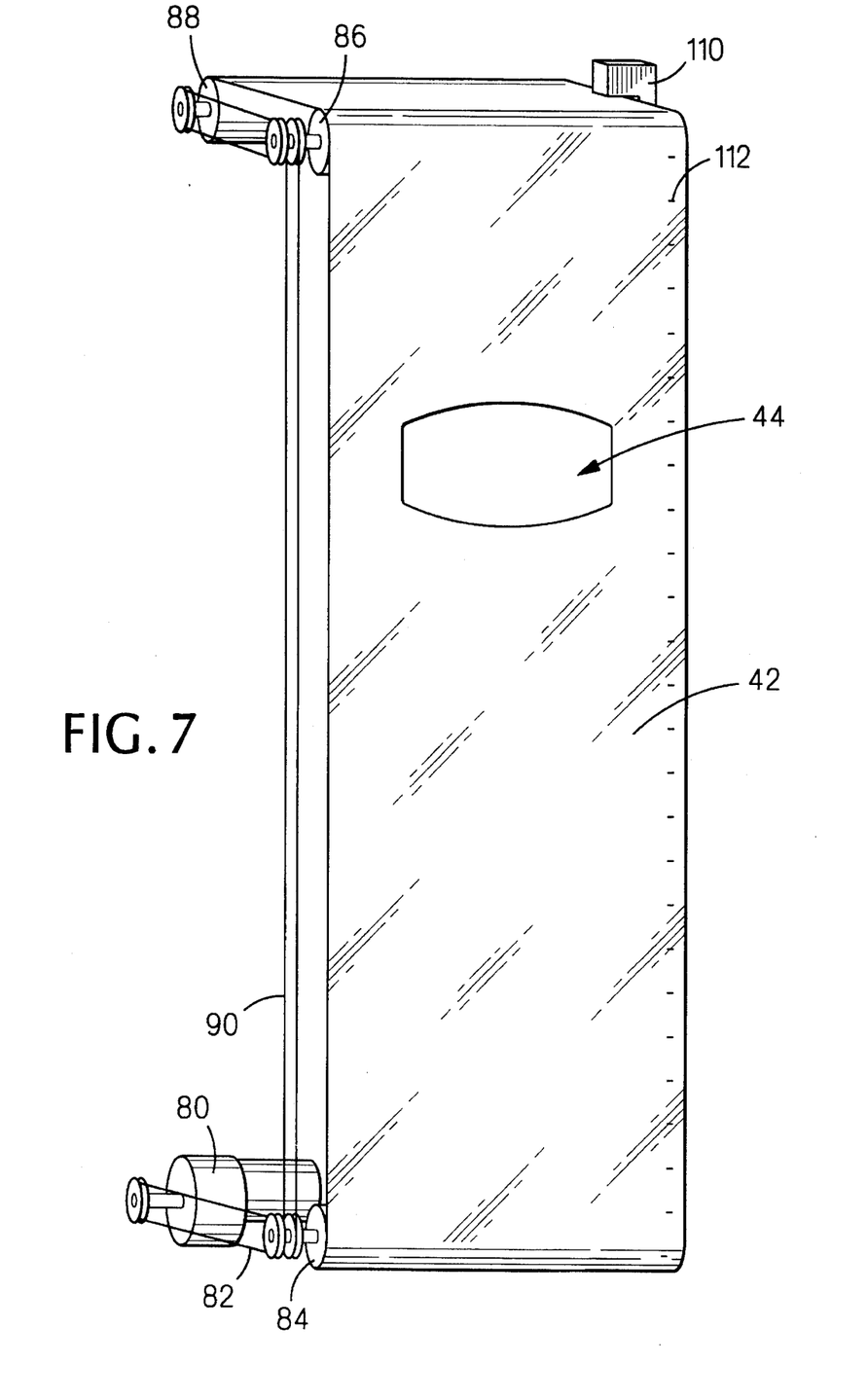
FIG. 7 is an isometric elevational view showing the sealing curtain of FIG. 2 and the drive mechanism therefor.

Referring now to FIG. 7, curtain 42 is driven by a mechanism which includes a DC drive gear motor 80, connected by a belt 82 to a head roller 84 to which head roller the curtain is firmly attached. A guide roller 86 turns curtain 42 ninety degrees to a tail roller 88 to which tail roller the curtain is also firmly attached. Tail roller 88 is driven by a belt 90 connected to head roller 84 and is, therefore, driven by motor 80.

Figure 8:
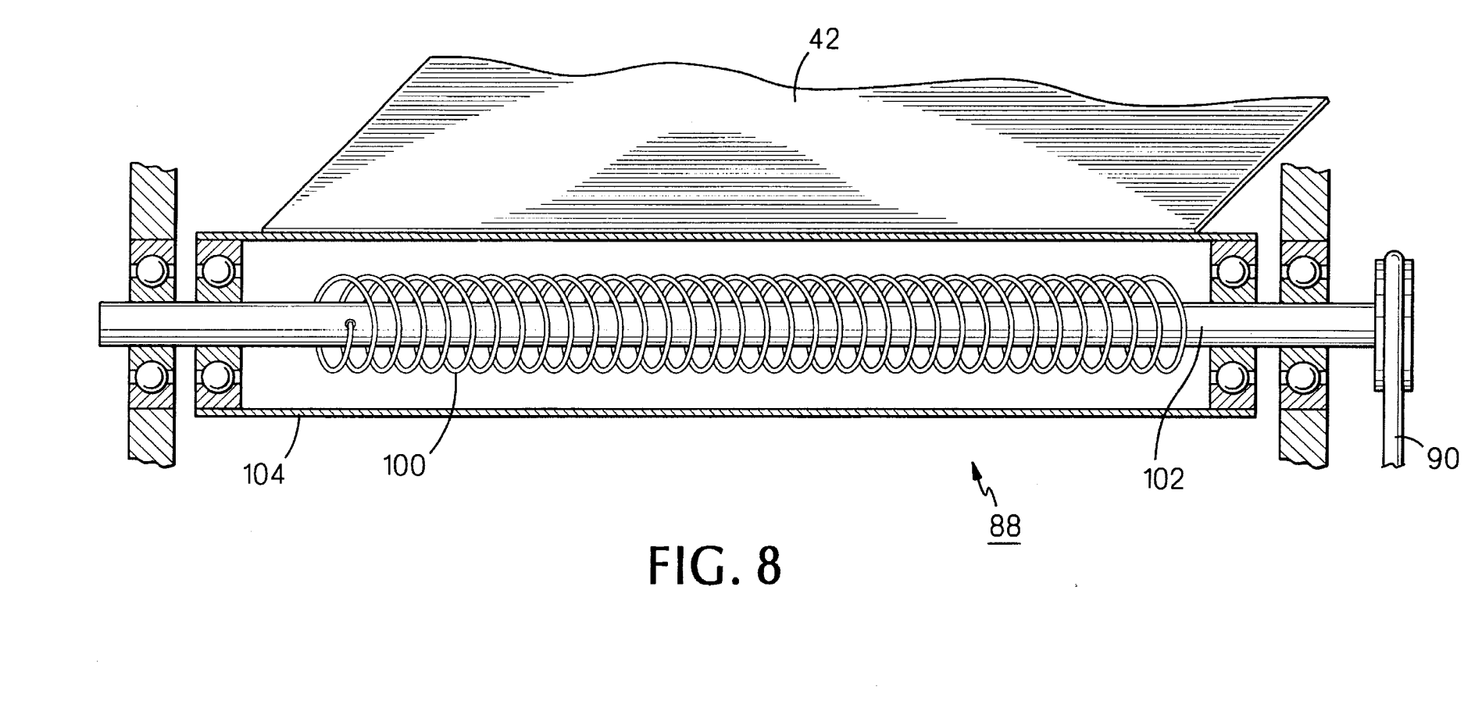
FIG. 8 is a cross-sectional view of a curtain tail roller for the sealing curtain of FIG. 7.

Referring also to FIG. 8, an internal wind up spring 100 is disposed within tail roller 88 and is connected between drive axle 102 and outer diameter 104 of the tail roller. Internal spring 100 serves to maintain a constant tension on curtain 42 and concurrently compensates for roll build up and build down, as the curtain winds and unwinds.

Referring back to FIG. 7, an edge of curtain 42 passes through a photodetector 110 that monitors the presence or absence of eye marks, as at 112, on that edge of the curtain. Eye marks 112 provide incremental encoding from a home position to allow the control circuit to position robotic access window 44 of curtain 42 at a selected vertical location.

Figure 6:
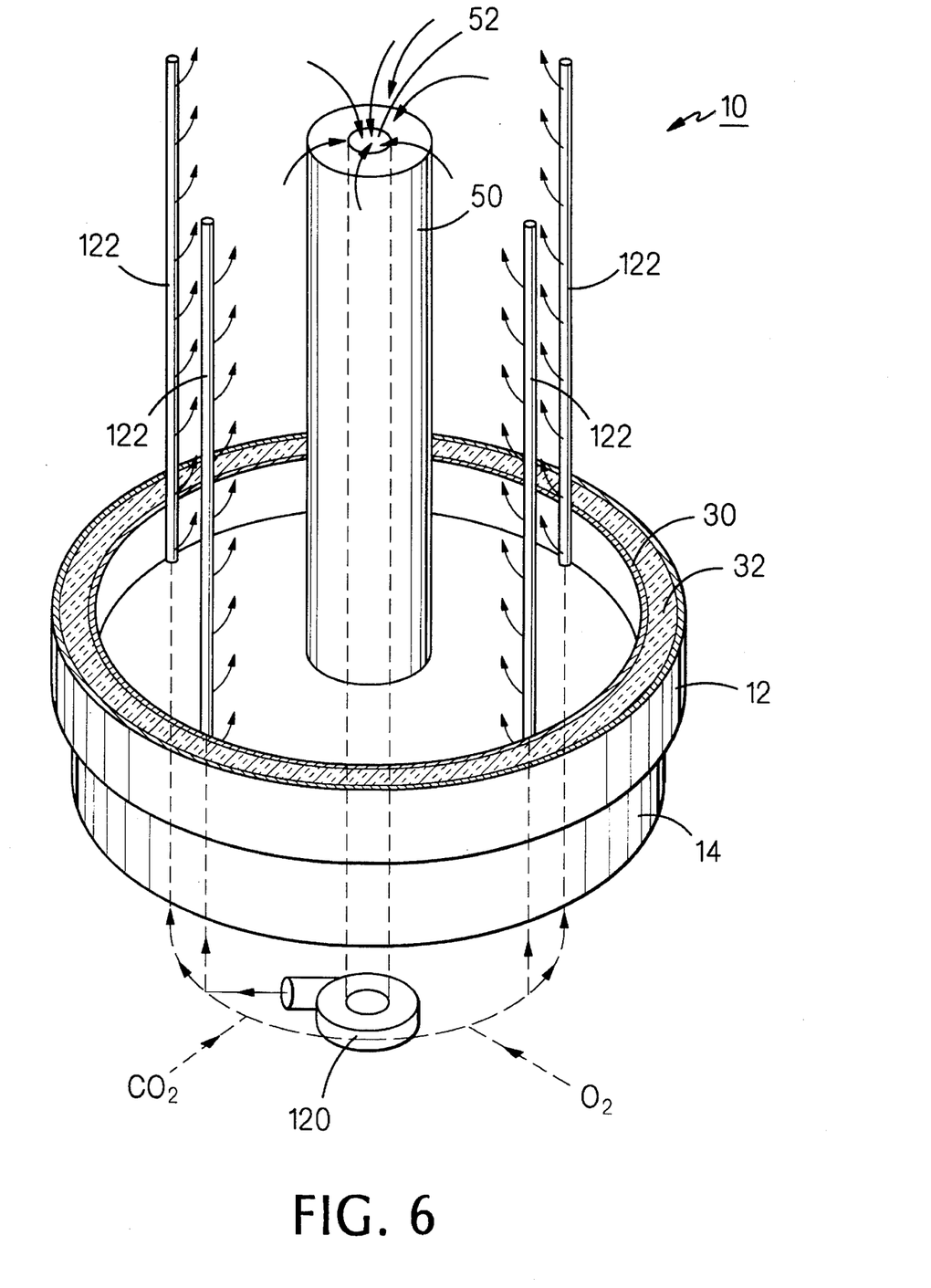
FIG. 6 is a fragmentary, cutaway isometric view of the incubator showing the air circulation pattern therein.

FIG. 6 illustrates the flow pattern of air in incubator 10. A small pressure blower 120 draws air from the interior of incubator 10 through center support tube 52, as indicated by the flow arrows, and discharges this air back into the incubator through four vertical sparger tubes 122, as is also indicated by the flow arrows, which sparger tubes are located on the inner perimeter of inner shell 30. Each sparger tube 122 has a vertical line of small holes (indicated by the flow arrows) that distribute the air flow uniformly from top to bottom in incubator 10. This circulating air flow prevents hot spots or temperature gradients from forming in incubator 10. If it is desired to modify the environment in incubator 10, constituents such as carbon dioxide or oxygen can be admitted in this circulating air stream.

Many assays require some form of agitation during incubation. This may be in the form of a gentle shaking to prevent particulate matter from settling out, or severe agitation to foster oxygenation, as in fermentation studies. By appropriately controlling drive motor 64 (FIG. 5), the entire central assembly of trays 46 can be oscillated. Both the amplitude and frequency of the oscillatory motion provided by drive motor 64 can be controlled to meet the shaking requirements.

Providing incubator 10 as a cylindrical enclosure within which there are stackable shelf assemblies 45 having shelves 46 extending outwardly from a central core, upon each shelf a bioassay tray may be disposed, provides for a high degree of concentration of a large number of trays in a compact volume. A column of stackable shelf assemblies 45 is selectively alignable with robotic access opening 40 and this circular arrangement of shelves 46 allows any one of the several vertical columns of shelves to be presented to one access line of a robotic arm (not shown). This has the effect of increasing the accessible space without increasing the arm's physical reach limitations. This feature is of especial importance on a pivot mounted robotic arm system, when the accessible space is very limited, and is important, as well, when the robotic arm moves along an aisle of such incubators. Curtain 42 with robotic access window 44 therein rolls to permit accessing a single shelf 46 at a time, while the curtain covers the balance of robotic access opening 40. The robotic hand (not shown) then reaches through robotic access window 44 to place or retrieve a sample plate. This provides a minimum of air interchange on the access, thus minimizing interference with the internal environment of incubator 10. During non-accessing times, curtain 42 is fully closed to maintain the interior environment.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A bioassay incubator for use with a robotic arm, said incubator comprising:
   (a) a housing;
   (b) a first plurality of linearly spaced apart shelves disposed within said housing, said shelves dimensioned to support thereon bioassay trays;
   (c) a robotic access opening defined in said housing and extending along said first plurality of shelves, through which robotic access opening said first plurality of shelves may be accessed by a robotic arm to place on, or to remove from, said bioassay trays;
   (d) sealing means disposed over and substantially sealing said robotic access opening;
   (e) said sealing means having defined therethrough a robotic access window, said robotic access window being positionable adjacent a selected one of said first plurality of shelves and being minimally dimensioned to permit said robotic arm to access said selected one of said shelves therethrough, while said sealing means otherwise substantially seals said robotic access opening to minimize disturbance of the interior environment of said incubator;
   (f) said sealing means comprising a flexible curtain, with said robotic access window therein selectively positionable in said robotic access opening by moving said flexible curtain back and forth across said robotic access opening;
   (g) one end of said flexible curtain being attached to a head roller disposed at one end of said robotic access opening and the other end of said flexible curtain being attached to a tail roller disposed at the other end of said robotic access opening; and
   (h) an electric motor attached to both said head and tail rollers to simultaneously rotate both said head and tail rollers.

2. A bioassay incubator, as defined in claim 1, further comprising:
   (a) said robotic access opening is a vertical opening defined in said housing;
   (b) shelves in said first plurality of shelves are vertically spaced apart;
   (c) at least a second plurality of vertically spaced apart shelves;
   (d) said first plurality of shelves and said at least a second plurality of shelves extend outwardly from a rotatable central core of said bioassay incubator; and
   (e) means to selectively rotate said central core so as to align either said first plurality of shelves or said at least a second plurality of shelves with said robotic access opening.

3. A bioassay incubator, as defined in claim 2, wherein said means to selectively rotate comprises an electric motor which can provide oscillating motion to agitate contents of trays disposed on said shelves.

4. A bioassay incubator, as defined in claim 3, wherein both frequency and amplitude of oscillations of said electric motor are selectively controlled.

5. A bioassay incubator, as defined in claim 2, wherein adjacent shelves of said first plurality of shelves and said at least a second plurality of shelves are spaced apart by spacer elements the thickness of which may be varied to accommodate therebetween bioassay trays of different heights.

6. A bioassay incubator, as defined in claim 1, further comprising: a torsion spring connected between an axle and a shell of one of said head and tail rollers so as to provide tension in said flexible curtain and to compensate for roll build up and build down as said flexible curtain winds and unwinds from said head and tail rollers.

* * * * *